United States Patent
Hossain et al.

(10) Patent No.: US 12,357,729 B1
(45) Date of Patent: Jul. 15, 2025

(54) ORGANIC BIOMATERIAL FOR BONE AND JOINT REPLACEMENT

(71) Applicant: IMAM MOHAMMAD IBN SAUD ISLAMIC UNIVERSITY, Riyadh (SA)

(72) Inventors: Abm Sharif Hossain, Riyadh (SA); Moniruddin Chowdhury, Kedah (MY); Fazliny Abdul Rahman, Petaling Jaya (MY)

(73) Assignee: IMAM MOHAMMAD IBN SAUD ISLAMIC UNIVERSITY, Riyadh (SA)

( * ) Notice: Subject to any disclaimer, the term of this patent is extended or adjusted under 35 U.S.C. 154(b) by 0 days.

(21) Appl. No.: 19/068,391

(22) Filed: Mar. 3, 2025

(51) Int. Cl.
*A61L 27/00* (2006.01)
*A61L 27/22* (2006.01)
*A61L 27/36* (2006.01)
*A61L 27/44* (2006.01)
*A61L 27/58* (2006.01)

(52) U.S. Cl.
CPC ......... *A61L 27/446* (2013.01); *A61L 27/3608* (2013.01); *A61L 27/3637* (2013.01); *A61L 27/3691* (2013.01); *A61L 2400/12* (2013.01); *A61L 2430/02* (2013.01)

(58) Field of Classification Search
CPC ............... A61L 27/446; A61L 27/3608; A61L 27/3637; A61L 27/3691; A61L 2400/12; A61L 2430/02
See application file for complete search history.

(56) References Cited

FOREIGN PATENT DOCUMENTS

| | | |
|---|---|---|
| CN | 116603113 A | 8/2023 |
| IN | 491251 B | 8/2019 |
| IN | 507078 B | 10/2022 |
| WO | 2009/134816 A9 | 11/2009 |

OTHER PUBLICATIONS

Hamisah Ismail, et al., "Bioactivity and Biocompatibility Properties of Sustainable Wollastonite Bioceramics from Rice Husk Ash/Rice Straw Ash: A Review", Materials, vol. 14, 5193, Sep. 10, 2021. 27 pages.

Bishwambhar Mishra, et al., "Valorization of agro-industrial biowaste to biomaterials: An innovative circular bioeconomy approach", Circular Economy, vol. 2, Aug. 19, 2023, 100050, 15 pages.

*Primary Examiner* — Ernst V Arnold
(74) *Attorney, Agent, or Firm* — Oblon, McClelland, Maier & Neustadt, L.L.P.

(57) ABSTRACT

An organic bone and joint replacement biomaterial includes a nanocomposite including a mixture of nanocellulose and nanostarch obtained from date seed, durum seed coat, moringa seed, fish bone, sheep jawbone, and olive seed. The organic bone and joint replacement biomaterial includes an antioxidant of one or more of a beet root dye, an ajwa date pigment, a blueberry dye, a black cumin seed pigment, a valvet apple peel dye. The organic bone and joint replacement biomaterial include an organic adhesive selected from the group of an *Acacia arabica* gel, agar gel media, and a moringa leaf extract. Further, it includes an organic composition of an arrowroot starch gel, pomegranate seed starch, and an animal-based glycerin. Further, it also includes an adhesive composition, a plasticizer and calcium oxide.

20 Claims, 8 Drawing Sheets

ORGANIC BIOMATERIAL FOR BONE AND JOINT REPLACEMENT

BACKGROUND

Technical Field

The present disclosure is directed to a biomaterial, more particularly, relates to an organic bone and joint replacement biomaterial and a method of preparing the biomaterial.

Description of Related Art

The "background" description provided herein is for the purpose of generally presenting the context of the disclosure. Work of the presently named inventors, to the extent it is described in this background section, as well as aspects of the description which may not otherwise qualify as prior art at the time of filing, are neither expressly nor impliedly admitted as prior art against the present invention.

Synthetic bone cement is a material used in orthopedic surgery, particularly in procedures such as joint replacement or vertebroplasty. Its primary function is to stabilize and hold implants in place or to repair bone fractures. It may be used as replacement of damaged bone or joint discs, such as hip discs, shoulder discs, spine discs, knee joint discs, and jaw discs for the medical and dental surgical use. It may be made mostly from metal, steel, ceramic, polymers, plastics, or combinations of all the materials.

The human bone is made up of varied compositions, about 30% flexible matrix and 70% bound minerals that are embedded with specialized bone cells. The distinct constitution of the bone allows it to be strong and hard while being lightweight. The bone matrix is composed of collagen (90%-95%) and ground substances. The collagen fibers provide elasticity and resistance to the structure. The matrix also contains calcium phosphate that hardens the bone structure. Internally, the matrix has a honeycomb-like structure that gives rigidity to bones.

Nowadays usually, synthetic or artificial materials are used in fitting or replacement of damaged or fractured bone or disc purposes after surgery for bone replacement in implants (making replacement in the original position). In surgery, a synthetic bone (steel or plastic) is used, which is very laborious, time-consuming, costly, and sometimes dangerous for the patient's bone decay and in that case second time surgery may be needed. Usually, artificial bone cement like PMMA and calcium phosphates have been widely used for the reconstruction of bone. Or replacement of decayed or damaged bone.

Using high-quality modern technology, bone cement may be made from synthetic plastic resins, ceramic composites, and metal alloys, which are still expensive and nonbiodegradable. Synthetic bone cement, like PMMA, may generate heat during hardening, potentially damaging surrounding tissues. It may degrade over time, leading to implant loosening or failure. Also, brittleness, lack of biological integration, and risk of infection, challenges in removal and potential allergic reactions all limit the long-term effectiveness of synthetic-based bone cement.

Each of the aforementioned synthetic bone cement material used suffers from one or more drawbacks hindering their adoption. Accordingly, one objective of the present disclosure is to provide a bone cement material that may circumvent the drawbacks, such as, low durability, brittleness, lack of biological integration, non-biodegradability, and high costs, of the materials known in the art.

SUMMARY

In an exemplary embodiment, an organic bone and joint replacement biomaterial is described. The organic bone and joint replacement biomaterial includes a nanocomposite including a mixture of nanocellulose and nanostarch obtained from date seed, durum seed coat, moringa seed, fish bone, sheep jawbone, and olive seed. The organic bone and joint replacement biomaterial includes an antioxidant including one or more of a beet root dye, an ajwa date pigment, a blueberry dye, a black cumin seed pigment, a velvet apple peel dye. The organic bone and joint replacement biomaterial further includes an organic adhesive selected from the group including *Acacia arabica* gel, agar gel media, and a moringa leaf extract. Furthermore, the organic bone and joint replacement biomaterial includes an organic composition including an arrowroot starch gel, pomegranate seed starch, and an animal-based glycerin. Further, the organic bone and joint replacement biomaterial includes an adhesive composition including at least one selected from the group including an okra gel, a cyanoacrylate adhesive, an aloe vera gel, a jackfruit latex, a wood apple glue, a *Lannea* sp. glue, and an aroid root gum. Still further, the organic bone and joint replacement biomaterial includes at least one plasticizer and calcium oxide.

In some embodiments, the nanocellulose is present in the nanocomposite in an amount of 45 (weight percent) wt. % to 65 wt. % relative to a total weight of the nanocomposite.

In some embodiments, the nanostarch is present in the nanocomposite in an amount of 30 wt. % to 55 wt. % relative to a total weight of the nanocomposite.

In some embodiments, the nanocellulose has an average particle size of 20 nanometers (nm) or less.

In some embodiments, the nanostarch has an average particle size of 18 nm or less.

In some embodiments, the organic bone and joint replacement biomaterial has an anthocyanin content of 95 milligram (mg) to 110 mg per 100 grams (g) of the organic bone and joint replacement biomaterial.

In some embodiments, the organic bone and joint replacement biomaterial has a carotene content of 1 mg to 10 mg per gram of the organic bone and joint replacement biomaterial.

In some embodiments, the plasticizer is at least one selected from the group including diethylhexyl phthalate, diisononyl phthalate, diisodecylphthalate, dioctyl adipate, tris(2-ethylhexyl) trimellitate, and polyvinyl chloride.

In some embodiments, the organic bone and joint replacement biomaterial has a calcium content of 5 parts per million (ppm) to 15 ppm relative to a total weight of the organic bone and joint replacement biomaterial.

In some embodiments, the organic bone and joint replacement biomaterial further includes at least one acrylate selected from the group including methyl methacrylate, ethyl acrylate, poly(methyl methacrylate), poly(methyl acrylate), polyacrylamide, polyacrylonitrile, poly(acrylic acid), trimethylolpropane triacrylate, hexanediol diacrylate, and pentaerythritol tetraacrylate.

In some embodiments, the organic bone and joint replacement biomaterial has calcium oxide (CaO) in an amount of 1 wt. % to 6 wt. % relative to a total weight of the organic bone and joint replacement biomaterial.

In some embodiments, the plasticizer is polyvinyl chloride.

In some embodiments, the organic bone and joint replacement biomaterial further includes poly(methyl methacrylate).

In some embodiments, the plasticizer is present in an amount of 1 wt. % to 10 wt. % relative to a total weight of the organic bone and joint replacement biomaterial.

In another exemplary embodiment, a method of producing the organic bone and joint replacement biomaterial is described. The method includes hydrolyzing a mixture of date seed, durum seed coat, moringa seed, fish bone, sheep jawbone, and olive seed with at least one inorganic acid to obtain the nanocomposite. Further the method includes combining the nanocomposite with the organic composition, the adhesive component, the calcium oxide, and the plasticizer to form the organic bone and joint replacement biomaterial. Still further, the method includes pressing the organic bone and joint replacement biomaterial into a mold and curing to form a bone or joint replacement.

In some embodiments, the inorganic acid is at least one selected from the group including hydrochloric acid, nitric acid, hydrobromic acid, sulfuric acid, hydrofluoric acid, and phosphorous acid.

In some embodiments, the inorganic acid is hydrochloric acid, sulfuric acid, and nitric acid.

In some embodiments, the method further includes drying the date seed, durum seed coat, moringa seed, fish bone, sheep jawbone, and olive seed at a temperature of 125° C. to 145° C. for 1 h to 4 h to obtain a powder including an olive seed, date seed, moringa seed, fish bone, and sheep jawbone.

In some embodiments, the curing is photocuring or thermal curing.

In some embodiments, the curing includes heating at a temperature of 100° C. to 160° C. for 3 h to 6 h.

The foregoing general description of the illustrative embodiments and the following detailed description thereof are merely exemplary aspects of the teachings of this disclosure and are not restrictive.

BRIEF DESCRIPTION OF THE DRAWINGS

A more complete appreciation of this disclosure and many of the attendant advantages thereof will be readily obtained as the same becomes better understood by reference to the following detailed description when considered in connection with the accompanying drawings, wherein.

DETAILED DESCRIPTION

When describing the present disclosure, the terms used are to be construed in accordance with the following definitions, unless a context dictates otherwise.

Embodiments of the present invention will now be described more fully hereinafter with reference to the accompanying drawings wherever applicable, in that some, but not all, embodiments of the disclosure are shown.

In the drawings, like reference numerals designate identical or corresponding parts throughout the several views. Further, as used herein, the words 'a,' 'an' and the like generally carry a meaning of 'one or more,' unless stated otherwise.

Furthermore, the terms 'approximately,' 'approximate,' 'about,' and similar terms generally refer to ranges that include the identified value within a margin of 20%, 10%, or preferably 5%, and any values therebetween.

As used herein, the term 'room temperature' refers to a temperature range of '25 degrees Celsius (° C.)±3° C. in the present disclosure.

A weight percent of a component, unless specifically stated to the contrary, is based on the total weight of the formulation or composition in which the component is included. For example, if a particular element or component in a composition or article is said to have 5 wt. %, it is understood that this percentage is in relation to a total compositional percentage of 100%.

The present disclosure is intended to include all hydration states of a given compound or formula, unless otherwise noted or when heating a material.

As used herein, the term "nanostarch" refers to starch that has been processed to a nanoscale size (e.g., at least one dimension that is 1,000 nm or less), typically through mechanical, chemical, or enzymatic methods, resulting in nanoparticles or nanocrystals of starch with enhanced properties such as increased surface area, solubility, and reactivity, making it suitable for use in a variety of applications, including as a reinforcing agent in nanocomposite materials.

As used herein, the term "nanocellulose" refers to a cellulose derivative that has been broken down into nanoscale fibers or crystals (e.g., at least one dimension that is 1,000 nm or less), typically through mechanical, chemical, or enzymatic processes, exhibiting unique properties such as high surface area, strength, and biocompatibility, making it suitable for use in various applications.

As used herein, the term "biomaterial" refers to any material that is designed to interact with biological systems, typically used for medical or healthcare applications, such as implants, prosthetics, or tissue engineering. Biomaterials can be synthetic or natural and are chosen for their biocompatibility, biodegradability, and ability to support or enhance biological functions, including the regeneration or repair of tissues and organs.

As used herein, the term "antioxidant" refers to a substance that inhibits oxidation or reactive oxygen species (ROS) formation, thereby protecting cells and tissues from oxidative damage. Antioxidants can neutralize free radicals and other harmful compounds, helping to prevent cellular damage and supporting overall health, and can be derived from natural sources such as plants, fruits, and vegetables, or synthesized for use in various applications, including in medical, food, and cosmetic products.

As used herein, the term "organic adhesive" refers to a naturally derived substance or compound that is used to bond or join materials together through non-synthetic means. Organic adhesives typically include substances such as plant-based gums, resins, proteins, and polysaccharides, which possess adhesive properties and are biodegradable and environmentally friendly, making them suitable for applications in packaging, medical devices, and other sustainable materials.

As used herein, the term "organic composition" refers to a mixture or combination of naturally derived substances, including plant-based, animal-based, or microbial materials, that possess organic chemical structures. These compositions may include proteins, carbohydrates, lipids, natural resins, and other organic compounds, and are often used in a variety of applications such as biomaterials, adhesives, coatings, and health products due to their biodegradability, biocompatibility, and sustainability.

As used herein, the term "adhesive" refers to a substance that is used to bond or stick two materials together by forming a strong interface between them. Adhesives can be composed of natural or synthetic materials and function by creating chemical, physical, or mechanical bonds. These substances are commonly used in various industries such as construction, manufacturing, medical, and packaging, and are selected based on their ability to provide a durable bond under specific conditions (e.g., moisture, temperature, or mechanical stress).

As used herein, the term "plasticizer" refers to a substance added to materials, particularly polymers, to increase their flexibility, workability, and durability by reducing their hardness and brittleness. Plasticizers typically function by lowering the glass transition temperature of a material, allowing it to become more pliable. They are commonly used in the production of plastics, coatings, and rubber, and can be organic or inorganic compounds such as phthalates, glycerin, or citrates.

As used herein, the term "average particle size" refers to the mean diameter of particles in a given sample, calculated by measuring the size distribution of particles and finding the central value, e.g., by number average. It is typically used to describe the size of powders, nanoparticles, or any particulate materials and is an important parameter in various fields such as materials science, pharmaceuticals, and nanotechnology. The average particle size is often determined through methods like dynamic light scattering (DLS), laser diffraction, or microscopy.

As used herein, the term "organic bone and joint replacement biomaterial" refers to a biocompatible material derived from natural, organic sources that is designed to replace or repair damaged bone or joint tissue. These biomaterials are typically made from organic compounds such as proteins, polysaccharides, or natural polymers, and are intended to integrate with the body's tissue while promoting healing, regeneration, and long-term functionality. They are often biodegradable, allowing the body to gradually replace them with new tissue, making them suitable for use in surgical procedures such as bone and joint replacement or reconstruction.

As used herein, the term "anthocyanin" refers to a class of water-soluble pigments found in various fruits, vegetables, and flowers that provide a red, blue, or purple color. Anthocyanins are a type of flavonoid and are known for their antioxidant properties, helping to neutralize free radicals and reduce oxidative stress. They are often used in food, cosmetics, and health-related applications due to their potential health benefits, including anti-inflammatory, anti-cancer, and heart-protective effects.

As used herein, the term "carotene" refers to a group of naturally occurring pigments, primarily found in fruits and vegetables, that give them their yellow, orange, and red colors. Carotene is a type of carotenoid, a class of compounds with antioxidant properties, and is particularly known for its role as a precursor to vitamin A in the body. Beta-carotene is the most common form, and it is important for vision, immune function, and skin health. Carotenes are widely used in dietary supplements, food colouring, and cosmetics due to their nutritional and health benefits.

An aspect of the present disclosure is directed to a nanostarch and nanocellulose-based organic nutritive nanocomposite bone cement biomaterial, incorporating animal bone powder and organic dyes as antioxidants, for use in the reconstruction and regrowth of damaged bone, providing a biodegradable and environmentally friendly alternative for tissue recovery post-surgery.

An organic bone and joint replacement biomaterial are described. The biomaterial includes a nanocomposite, an antioxidant, an organic adhesive, an organic composition, an adhesive, at least one plasticizer and calcium oxide. The nanocomposite includes a mixture of nanocellulose and nanostarch. In some embodiments, nanocellulose and nanostarch can be obtained from various natural sources, including banana peel, corn husk, rice husk, wheat straw, sugarcane bagasse, potato peel, cassava peel, sweet potato, mango seed kernel, pineapple peel, apple pomace, coconut husk, soybean hull, pea pod, orange peel, lemon peel, jackfruit seed, papaya peel, barley husk, oat hull, grape pomace, tamarind seed, guava peel, aloe vera rind, durian rind, bamboo shoot waste, coffee husk, tea waste, pomegranate peel, and cotton stalk, date seed, durum seed coat, moringa seed, fish bone, sheep jawbone, and olive seed. In a preferred embodiment, nanocellulose is obtained from olive seeds and nanostarch is obtained from moringa seed and date seeds.

In some embodiments, nanocellulose is present in the nanocomposite in an amount of 45 to 65 wt. %, preferably 45-50 wt. %, preferably 48-55 wt. %, preferably 50-60 wt. %, preferably 52-58 wt. %, preferably 55-65 wt. % relative to a total weight of the nanocomposite. In a preferred embodiment, nanocellulose is present in the nanocomposite in an amount of 50.0%+0.3 wt. % relative to a total weight of the nanocomposite. In some embodiments, the nanostarch is present in the nanocomposite in an amount of 30 to 55 wt. %, preferably 30-35 wt. %, preferably 32-40 wt. %, preferably 35-45 wt. %, preferably 38-50 wt. %, preferably 40-55 wt. % relative to a total weight of the nanocomposite. In a preferred embodiment, the nanostarch is present in the nanocomposite in an amount of 30.0%±0.2 wt. % relative to a total weight of the nanocomposite.

In some embodiments, the nanocellulose has an average particle size of 20 nm, preferably 25 nm, preferably 30 nm, preferably 35 nm, preferably 40 nm, preferably 45 nm, preferably 50 nm or less. In a preferred embodiment, nanocellulose has an average particle size of 16 nm. In some embodiments, nanostarch has an average particle size of 18 nm, preferably 20 nm, preferably 25 nm, preferably 30 nm, preferably 35 nm, preferably 40 nm, preferably 45 nm, preferably 50 nm or less. In a preferred embodiment, nanostarch has an average particle size of 14 nm.

In some embodiments, an antioxidant may include but is not limited to green tea extract, pomegranate extract, turmeric extract, ginger extract, garlic extract, cinnamon extract, rosemary extract, grape seed extract, olive leaf extract, hibiscus extract, spinach extract, kale extract, artichoke extract, broccoli extract, acai berry extract, goji berry extract, cranberry extract, cherry extract, raspberry extract, strawberry extract, blackberry extract, turmeric powder, cocoa powder, apple extract, citrus bioflavonoids, matcha powder, nettle leaf extract, milk thistle extract, elderberry extract, and parsley extract. In a preferred embodiment, an antioxidant includes one or more of a beet root dye, an ajwa date pigment, a blueberry dye, a black cumin seed pigment, a velvet apple peel dye.

In some embodiments, an organic adhesive may be selected from the group including, but not limited to, guar gum, xanthan gum, chitosan, pectin, corn starch, potato starch, rice starch, sodium alginate, methyl cellulose, carboxymethyl cellulose, honey, aloe vera gel, wheat gluten, gum arabic, glycerin, beeswax, shellac, casein, gelatin, starch derivatives, cellulose acetate, pullulan, tragacanth gum, tamarind gum, locust bean gum, guar gum derivatives, polyvinyl alcohol, polyacrylic acid, and hydroxypropyl cellulose. In a preferred embodiment, the organic adhesive is selected from the group including *Acacia arabica* gel, agar gel media, and a moringa leaf extract.

In some embodiment, an organic composition includes but is not limited to aloe vera gel, guar gum, xanthan gum, pectin, potato starch, rice starch, cornstarch, agar-agar, chitosan, carboxymethyl cellulose, glycerin (plant-based), gum arabic, honey, turmeric powder, spirulina extract, coconut oil, olive oil, soy protein, wheat germ oil, shea butter, beeswax, acai berry extract, blueberry extract, rosehip oil, almond oil, cocoa butter, vitamin E, sea buckthorn oil, castor oil, avocado oil, jojoba oil, and hemp oil. In a preferred embodiment, the organic composition includes arrowroot starch gel, pomegranate seed starch, and an animal-based glycerin.

In some embodiments, an adhesive composition includes at least one selected from, but not limited, to guar gum, xanthan gum, chitosan, pectin, corn starch, potato starch, rice starch, sodium alginate, methyl cellulose, carboxymethyl cellulose, honey, wheat gluten, gum arabic, glycerin, beeswax, shellac, casein, gelatin, starch derivatives, cellulose acetate, pullulan, tragacanth gum, tamarind gum, locust bean gum, polyvinyl alcohol, polyacrylic acid, hydroxypropyl cellulose, guar gum derivatives, gelatinized starch, agar-agar, and cassava gum. In a preferred embodiment, an adhesive composition includes at least one selected from okra gel, a cyanoacrylate adhesive, an aloe vera gel, a jackfruit latex, a wood apple glue, a *Lannea* sp. glue, and an aroid root gum.

In some embodiments, the organic bone and joint replacement biomaterial includes at least one acrylate selected from the group consisting of methyl methacrylate, ethyl acrylate, poly(methyl methacrylate), poly(methyl acrylate), polyacrylamide, polyacrylonitrile, poly(acrylic acid), trimethylolpropane triacrylate, hexanediol diacrylate, and pentaerythritol tetraacrylate. In a preferred embodiment, the acrylate includes poly(methyl methacrylate).

In some embodiments, the plasticizer may include, but is not limited to, dibutyl phthalate, dioctyl phthalate, dimethyl phthalate, butyl benzyl phthalate, tricresyl phosphate, triphenyl phosphate, acetyl tributyl citrate, acetyl triethyl citrate, epoxidized soybean oil, castor oil, glycerol, sorbitol, polyethylene glycol, polypropylene glycol, dioctyl adipate, di(2-ethylhexyl) sebacate, tributyl citrate, dibutyl sebacate, 2-ethylhexanol, diisononyl phthalate, diisodecyl phthalate, butyl stearate, polyethylene glycol-400, propylene glycol, butylene glycol, diethylene glycol, triethylene glycol, and isopropyl myristate. In some embodiments, the plasticizer is at least one of diethylhexyl phthalate, diisononyl phthalate, diisodecylphthalate, dioctyl adipate, tris(2-ethylhexyl)trimellitate, and polyvinyl chloride. In a preferred embodiment, the plasticizer is polyvinyl chloride.

In some embodiments, the plasticizer is present in an amount ranging from 1 to 10 wt. %, preferably 1-3 wt. %, preferably 2-5 wt. %, preferably 3-7 wt. %, preferably 4-8 wt. %, preferably 6-10 wt. % relative to a total weight of the organic bone and joint replacement biomaterial. In a preferred embodiment, the plasticizer is present in an amount of 5 wt. % relative to a total weight of the organic bone and joint replacement biomaterial.

In some embodiments, CaO is present in an amount ranging from 1 to 6 wt. %, preferably 1-2 wt. %, preferably 2-4 wt. %, preferably 3-5 wt. %, preferably 1.5-3.5 wt. %, preferably 4-6 wt. % relative to a total weight of the organic bone and joint replacement biomaterial. In a preferred embodiment, CaO is present in an amount of 2 wt. % relative to a total weight of the organic bone and joint replacement biomaterial.

In some embodiments, the organic bone and joint replacement biomaterial has a calcium content ranging from 5 to 15 parts per million (ppm), preferably 5-8 ppm, preferably 6-10 ppm, preferably 7-12 ppm, preferably 8-14 ppm, preferably 10-15 ppm relative to a total weight of the organic bone and joint replacement biomaterial. In a preferred embodiment, the organic bone and joint replacement biomaterial has a calcium content of 10.0±0.22 parts per million (ppm) relative to a total weight of the organic bone and joint replacement biomaterial.

In some embodiments, the organic bone and joint replacement biomaterial has an anthocyanin content ranging from 95 to 110 mg per 100 g, preferably 95-98 mg/100 g, preferably 96-102 mg/100 g, preferably 98-105 mg/100 g, preferably 100-108 mg/100 g, preferably 103-110 mg/100 g of the organic bone and joint replacement biomaterial. In a preferred embodiment, the organic bone and joint replacement biomaterial has an anthocyanin content of 102 mg per 100 g of the organic bone and joint replacement biomaterial.

In some embodiments, the organic bone and joint replacement biomaterial has a carotene content ranging from 1 to 10 mg per gram, preferably 1-3 mg/100 g, preferably 2-5 mg/100 g, preferably 4-7 mg/100 g, preferably 5-9 mg/100 g, preferably 6-10 mg/100 g of the organic bone and joint replacement biomaterial. In a preferred embodiment, the organic bone and joint replacement biomaterial has a carotene content of 3.4 mg per gram of the organic bone and joint replacement biomaterial.

Figure 1:
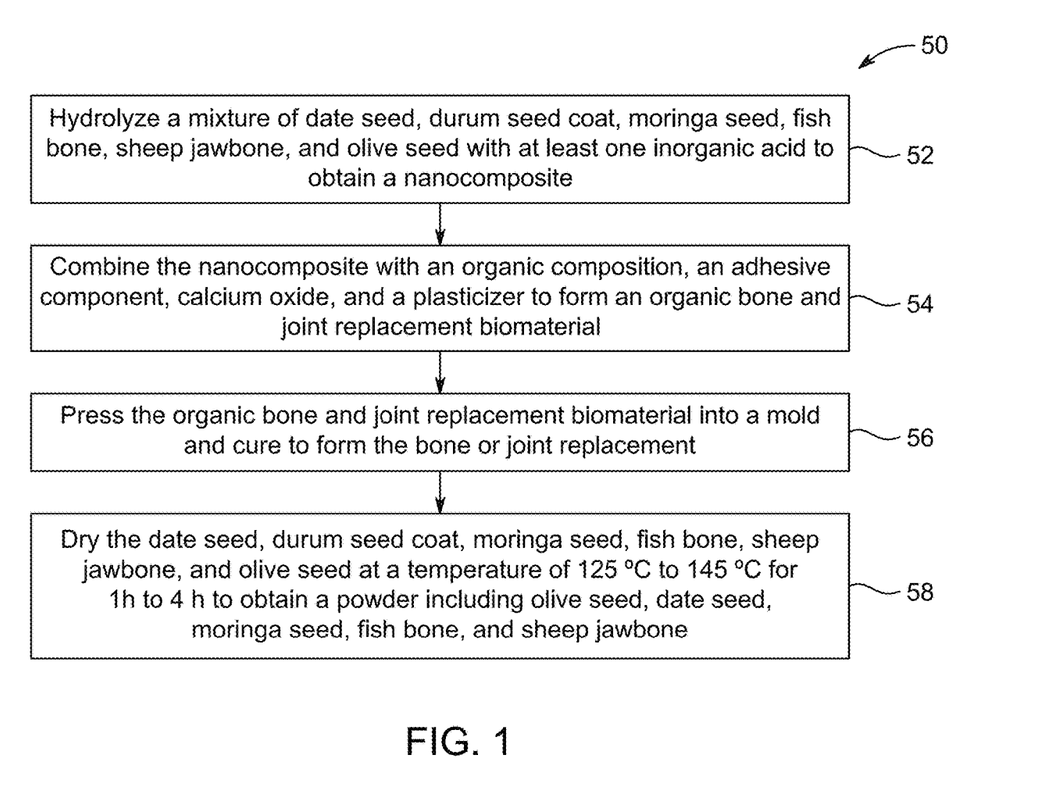
FIG. 1 is a schematic flow chart of a method of producing an organic bone and joint replacement biomaterial, according to certain embodiments.

FIG. 1 illustrates a schematic flow chart of a method 50 of preparing the organic bone and joint replacement biomaterial. The order in which the method 50 is described is not intended to be construed as a limitation, and any number of the described method steps can be combined to implement the method 50. Additionally, individual steps may be removed or skipped from the method 50 without departing from the spirit and scope of the present disclosure.

At step 52, the method 50 includes hydrolyzing a mixture of date seed, durum seed coat, moringa seed, fish bone, sheep jawbone, and olive seed with at least one inorganic acid to obtain the nanocomposite. In some embodiment, the inorganic acid may include but is not limited to phosphoric acid, boric acid, hydrofluoric acid, carbonic acid, perchloric acid, chloric acid, hypochlorous acid, hydrobromic acid, bromic acid, iodic acid, periodic acid, hydroiodic acid, chromic acid, permanganic acid, selenic acid, selenous acid, telluric acid, tellurous acid, silicic acid, tungstic acid, molybdic acid, stannic acid, stannous acid, vanadic acid, arsenic acid, arsenous acid, antimonic acid, antimonous acid, and pyrophosphoric acid. In some embodiment, the inorganic acid is at least one selected from the group including of hydrochloric acid, nitric acid, hydrobromic acid, sulfuric acid, hydrofluoric acid, and phosphorous acid. In a preferred embodiment, inorganic acid is hydrochloric acid, sulfuric acid, and nitric acid.

The method further includes drying the date seed, durum seed coat, moringa seed, fish bone, sheep jawbone, and olive seed at a temperature of 125 to 145° C. for 1 to 4 h to obtain a powder comprising olive seed, date seed, moringa seed, fish bone, and sheep jawbone.

In some embodiments, the method of drying the date seed, durum seed coat, moringa seed, fish bone, sheep jawbone, and olive seed is performed at a temperature ranging from 125 to 145° C., preferably 125-130° C., preferably 128-135° C., preferably 130-140° C., preferably 132-142° C., preferably 135-145° C. In a preferred embodiment, the drying is done at a temperature of 137° C. In some embodiments, the method of drying the date seed, durum seed coat, moringa seed, fish bone, sheep jawbone, and olive seed is carried out for 1 to 4 h, preferably 1-1.5 h, preferably 1.5-2.5 h, preferably 2-3 h, preferably 2.5-3.5 h, preferably 3-4 h. In a preferred embodiment, the method of drying the date seed, durum seed coat, moringa seed, fish bone, sheep jawbone, and olive seed is carried out for 2.5 hours.

At step 54, the method 50 includes combining the nanocomposite with the organic composition, the adhesive component, the calcium oxide, and the plasticizer to form the organic bone and joint replacement biomaterial.

At step 56, the method 50 includes pressing the organic bone and joint replacement biomaterial into a mold and curing to form a bone or joint replacement. In some embodiments, the curing may include but is not limited to chemical curing, moisture curing, UV curing, anaerobic curing, oxidative curing, solvent evaporation curing, plasma curing, electron beam curing, microwave curing, enzymatic curing, radiation curing, ionic curing, catalytic curing, peroxide curing, redox curing, hydrothermal curing, humidity curing, pressure curing, infrared curing, ultrasonic curing, vapor phase curing, electrochemical curing, acid-catalyzed curing, base-catalyzed curing, latent heat curing, isothermal curing, cold curing, ambient curing, multi-stage curing, and self-curing. In a preferred embodiment, the curing is photocuring or thermal curing.

In some embodiments, the curing includes heating the organic bone and joint replacement biomaterial at a temperature ranging from 100 to 160° C., preferably 100-110° C., preferably 115-130° C., preferably 120-140° C., preferably 130-150° C., preferably 145-160° C. In some embodiments, the curing includes heating the organic bone and joint replacement biomaterial at a temperature ranging from 3 to 6 h, preferably 3-3.5 h, preferably 3.5-4.5 h, preferably 4-5 h, preferably 4.5-5.5 h, preferably 5-6 h.

The following examples are provided solely for illustration and are not to be construed as limitations of the present disclosure, as many variations thereof are possible without departing from the spirit and scope of the present disclosure.

EXAMPLES

The following examples demonstrate an organic bone and joint replacement biomaterial as described herein. The examples are provided solely for illustration and are not to be construed as limitations of the present disclosure, as many variations thereof are possible without departing from the spirit and scope of the present disclosure.

Example 1: Materials Used and Method of Preparation

In the present disclosure, a process may be described in various stages. The process includes heating, drying and/or pyrolysis of the combination of the samples (date seed, durum seed coat nanocellulose, olive seed nanocellulose, fish bone, and sheep jawbone) at 137° C. in the oven for 2.5 hours. Further, acid hydrolysis, at 83%, 87%, and 93% was used in the experiment to convert microparticles to nanoparticles of date seed (83%), olive seed cellulose and durum seed coat cellulose, [83% hydrochloric acid (HCl), 87% nitric acid ($HNO_3$) and 93% sulfuric acid ($H_2SO_4$)] and fish bone and sheep jawbone (93% $H_2SO_4$). Still further, plasticizer polyvinyl chloride (PVC) (5%), poly methyl methacrylate (PMMA) bone cement (10%), calcium oxide (CaO) (2%) oyster shell nanoparticle (2%), cyanoacrylate adhesive (3%), starch (3%), arrowroot gel (2%), agar gel media (2%), alginate (2%) pomegranate peel starch (2%) were used. Still further, a mixture of organic substances (aloe vera gel, okra gel, aroids peel gel, *acacia arabica* gel, wood apple placenta glue, natural glue [fresh gum (*Lannea* sp)], jackfruit latex, glycerin from animal sources (chicken toes) were also used. Furthermore, the process includes nutritive substances like moringa leaf extract (which contains antioxidants and minerals), fish bone powder as mineral sources, and animal jaw (sheep) bone powder as calcium sources. Organic pigments or dyes such as antioxidants (velvet apple dye, beetroot dye, ajwa date coating dye, black cumin seed dye) pigments or dyes such as anthocyanin) were also used.

Example 2: Determination of pH, Antioxidant, Cellulose, and Starch in the Samples The pH, antioxidant, cellulose, and starch determination of the nanocomposite biomaterial of the present disclosure was determined, and the values were compared to synthetic bone cement available in the market. The quantitative determination of pH, antioxidant, cellulose, and starch determination was carried out using methods known in the art. The results of the study are depicted in Table 1.

TABLE 1 pH, antioxidant, cellulose, and starch determination (Mean ± SE (standard Error, n = 3)).

| Materials | pH determination | Starch determination | Cellulose determination | Anthocyanin as antioxidant (mg/100 g) |
|---|---|---|---|---|
| Nanocomposite bone cement | 7.7 ± 0.04 | 39.0% ± 0.2 | 50.0% ± 0.3 | 102 |
| Synthetic bone cement | Alkaline ≥ 7 | It is zero if from gas or oil; if from starch sample, it is 10-40%. | It is zero if from gas or oil, if from cellulose sample it is 20-50%. | 0 |

Example 3: Nanostarch, Nanocellulose, Carotene, Measurement

The particle size of the nanostarch, nanocellulose, and carotene was measured by scanning electron microscopy (SEM), and the results indicate that the average nanoparticle size of nanocomposite biomaterial was 15 nanometres (nm) (nanostarch: 14 nm and nanocellulose: 16 nm); in comparison, the nanoparticle size range for standard synthetic bone cement, which typically falls between 1 and 100 nm. The data indicate that the nanocomposite biomaterial has a finer particle size, potentially offering distinct properties and advantages in bone and joint replacement applications.

TABLE 2

Measurement of nanostarch and nanocellulose by SEM

| Materials | Nanostarch size | Nanocellulose size | Carotene content mg/g |
|---|---|---|---|
| Nanocomposite bone cement | 14 nm | 16 nm | 3.4 |
| Synthetic bone cement | 1-100 nm (standard) | 1-100 nm (standard) | 0 |

Example 4: Moisture, Odor, and Viscosity Test in Dental Filler Biomaterial (as ASTM D3801)

The nanocomposite biomaterial prepared was further evaluated to measure its ability to absorb moisture. The tests to determine water absorption were carried out in accordance with ASTM D3801. The purpose of ASTM D3801 is to determine the water absorption rate by immersing the specimen (nanocomposite bone cement) in water for a specific period. In the test, the nanocomposite biomaterial absorbed 10% water, and that synthetic bone cement absorbed 1%-30% water. Water absorption was calculated by determining the percentage increase in weight of the sample following the experiment to characterize the attribute. The results of the study are depicted in Table 3. It may be observed that the water absorption for the nanocomposite biomaterial prepared by the present disclosure is very low compared to synthetic bone cement, indicating a water-resistant property.

TABLE 3

Determination of moisture, odor, and viscosity test in nanocomposite bone cement

| Materials | Moisture percent | Viscosity (cSt) | Odor |
|---|---|---|---|
| Nanocomposite bone cement | 10% | 28 | Low odor |
| Synthetic bone cement by ASTM D3801 | Maximum 1%-30% | 15-30 | Low odor |

Example 5: Determination of Chemical Element Test in Nanocomposite Bone Cement Biomaterial Chemical element tests, such as sodium (Na), potassium (K), carbonate ($CO_3^-$), chloride (Cl), calcium (Ca), silicon (Si), iron (Fe), lead (Pb), copper (Cu), aluminum (Al), tin (Sn), zinc (Zn), nickel (Ni), magnesium (Mg), phosphorus (P), and manganese (Mn) were determined using the EN (166) [European Norm, 166] standardization. Similar results were exhibited when compared to synthetic bone cement. All the elements showed values under the standard. The results of the study are depicted in Table 4.

TABLE 4

Determination of chemical element test in dental filler biomaterials (Mean ± standard error (SE, n = 3))

| Chemical Elements (ppm) | Nanocomposite dental Filler (ppm) | Synthetic dental filler by EN (European Standard EN166) |
|---|---|---|
| K | 9.5 ± 0.3 | 10 |
| Na | 4.4 ± 0.3 | 5 |
| Cl | 0.47 ± 0.01 | 2 |
| $CO_3^-$ | 165 ± 1.4 | 440-5 |
| Ca | 10.0 ± 0.22 | 10 |
| Si | 2.6 ± 0 | 5 |
| Fe | 1.6 ± 0 | 5 |
| Cu | 0.38 ± 0 | 5 |
| Al | 1.6 ± 0 | 5 |
| Zn | 3.7 ± 0 | 5 |
| Ni | 0.03 ± 0 | 5 |
| Mg | 2 ± 0 | 5 |
| P | 9.0 ± 0 | 10 |
| Mn | 3 ± 0 | 5 |

Example 6: Effects of Organic Nanocomposite and Synthetic Materials on Sheep Bone The nanocomposite bone cement prepared was further evaluated on sheep bone to assess the hours required for drying and fitting damaged bone. The hours required for drying and fitting damaged bone using synthetic bone cement is around 2.5 hours, with a possibility of infection. Hours required for drying and fitting damaged bone using the organic nanocomposite bone cement of the present disclosure is around 1.5 hours, with no possibility of any infection. The data clearly indicates that organic nanocomposite bone cement may be a good replacement for bone and joint repair.

TABLE 5

Effects of organic nanocomposite and synthetic bone cement on sheep bone

| Samples | Hours required for drying and fitting damaged bone | Percent dried | Infection % |
| --- | --- | --- | --- |
| Synthetic bone cement | 2.5 ± 0.1 | 100 ± 0.4 | Possibility |
| Organic nanocomposite bone cement | 1.5 ± 0.2 | 100 ± 0.3 | Infection 0% |

Figure 2A:
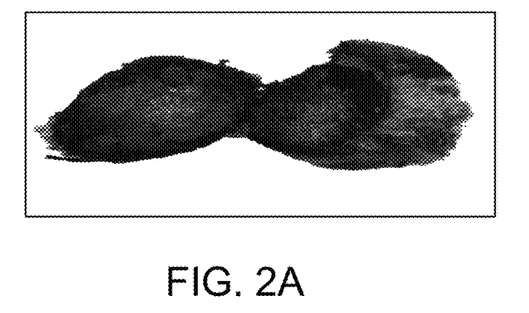
FIG. 2A is an image depicting black palm seed coat, according to certain embodiments.
Figure 2B:
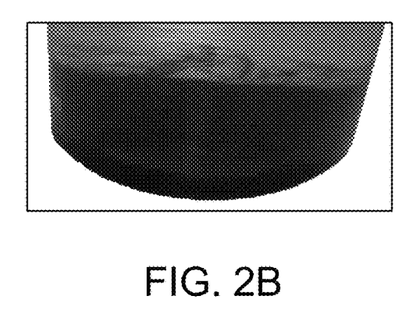
FIG. 2B is an image depicting black palm seed coat nanocellulose by acid hydrolysis, according to certain embodiments.
Figure 2C:
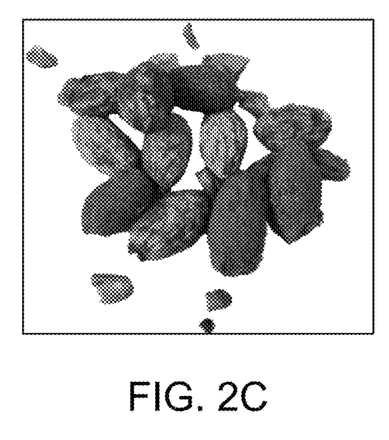
FIG. 2C is an image depicting olive seed and olive seed grinding, according to certain embodiments.
Figure 2D:
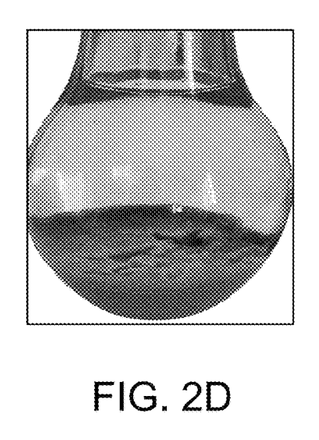
FIG. 2D is an image depicting olive seed nanocellulose by acid hydrolysis, according to certain embodiments.
Figure 2E:
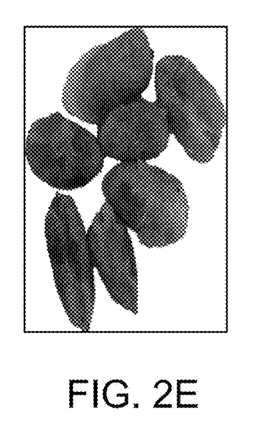
FIG. 2E is an image depicting dates seed, according to certain embodiments.
Figure 2F:
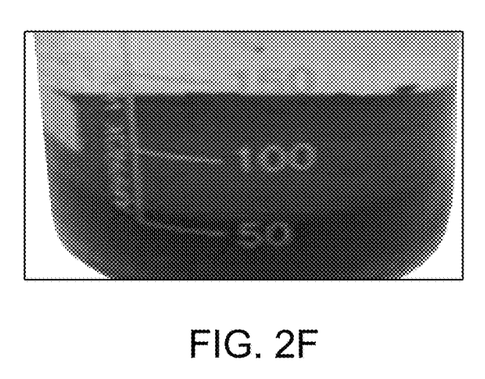
FIG. 2F is an image depicting date seed by acid hydrolysis, according to certain embodiments.
Figure 2G:
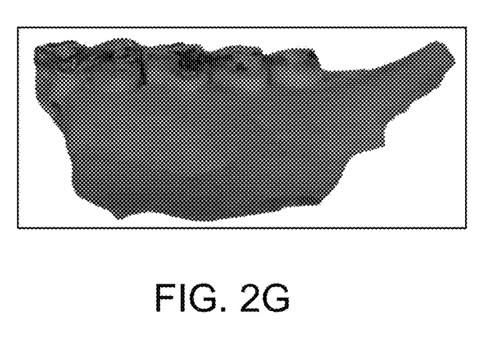
FIG. 2G is an image depicting sheep jawbone, according to certain embodiments.
Figure 2H:
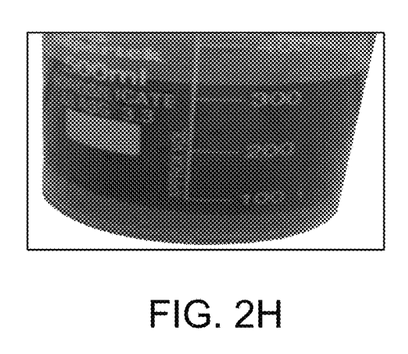
FIG. 2H is an image depicting sheep jawbone by acid hydrolysis, according to certain embodiments.
Figure 2I:
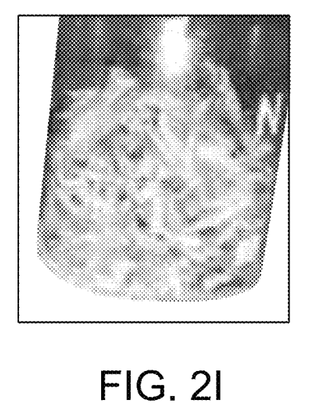
FIG. 2I is an image depicting chicken toes, according to certain embodiments.
Figure 2J:
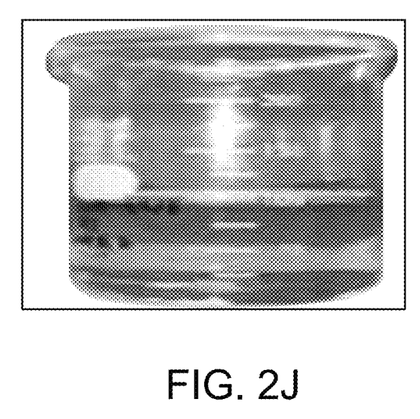
FIG. 2J is an image depicting glycerin, according to certain embodiments.
Figure 2K:
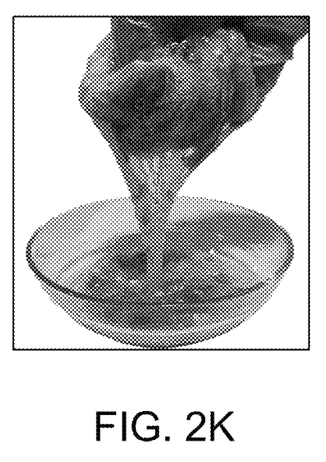
FIG. 2K is an image depicting okra gel, according to certain embodiments.
Figure 2L:
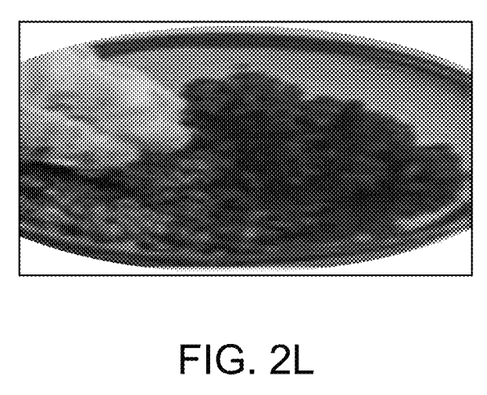
FIG. 2L is an image depicting different moringa seed, according to certain embodiments.
Figure 2M:
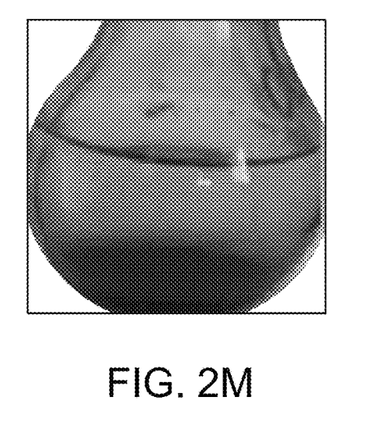
FIG. 2M is an image depicting different moringa seed nanostarch, according to certain embodiments.
Figure 2N:
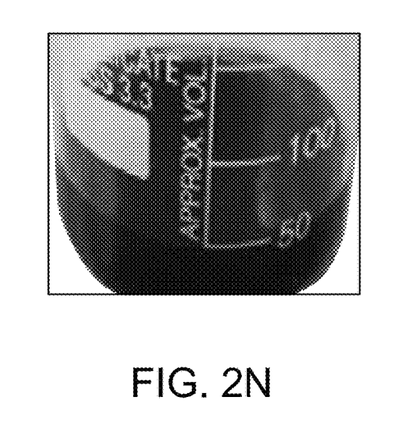
FIG. 2N. is an image depicting organic black seed and black seed organic dye, according to certain embodiments.
Figure 2O:
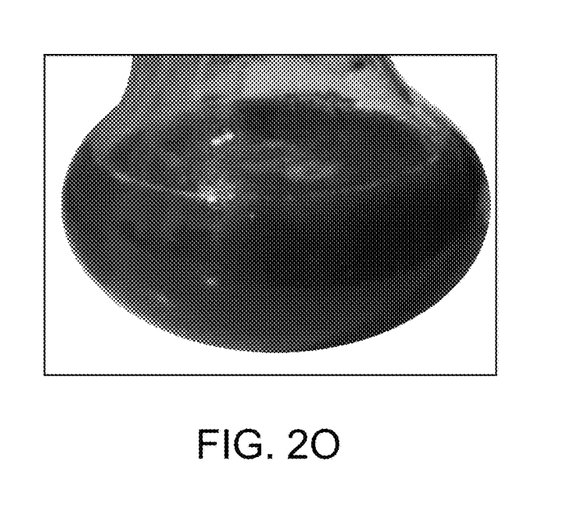
FIG. 2O is an image depicting valvet apple dye, according to certain embodiments.
Figure 2P:
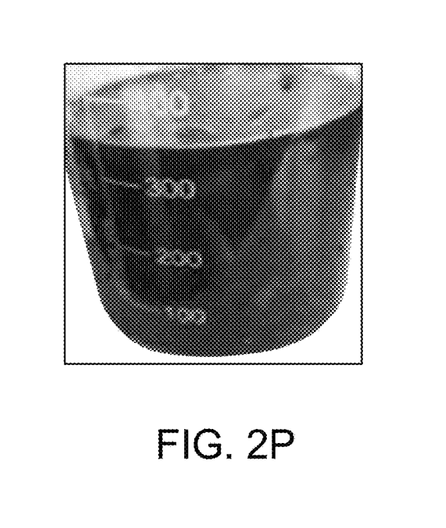
FIG. 2P is an image depicting beetroot peels dye, according to certain embodiments.
Figures 2Q, 2R:
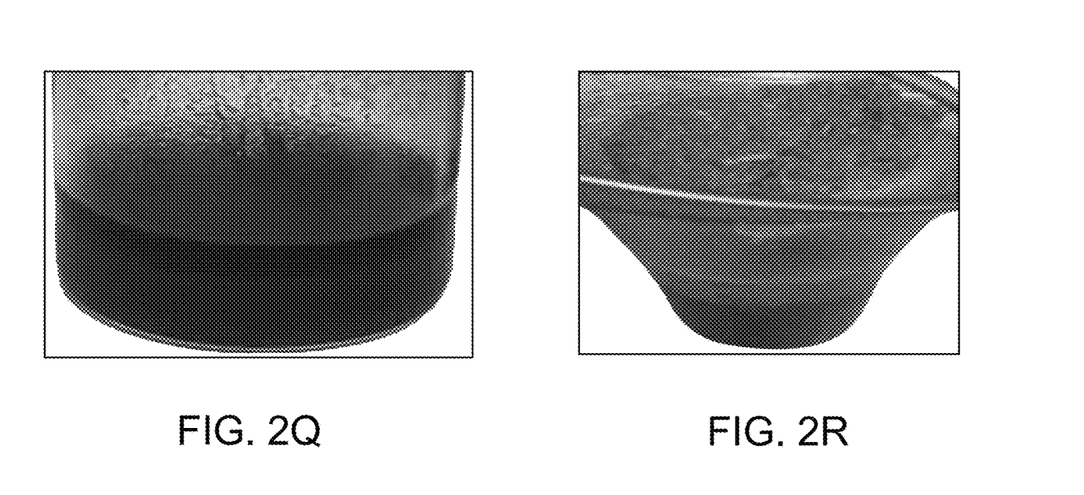
FIG. 2Q is an image depicting ajwa dates and dates dye, according to certain embodiments.
FIG. 2R is an image depicting olive leaf extract, according to certain embodiments.
Figures 2S, 2T:
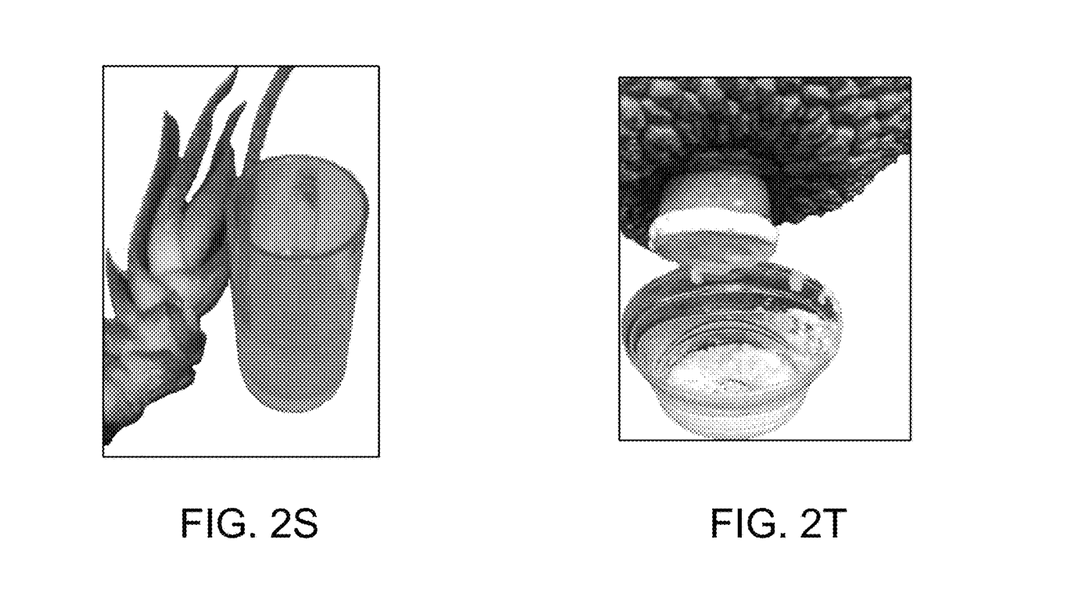
FIG. 2S is an image depicting aloe vera leaf and gel, according to certain embodiments.
FIG. 2T is an image depicting jackfruit latex, according to certain embodiments.
Figure 2U:
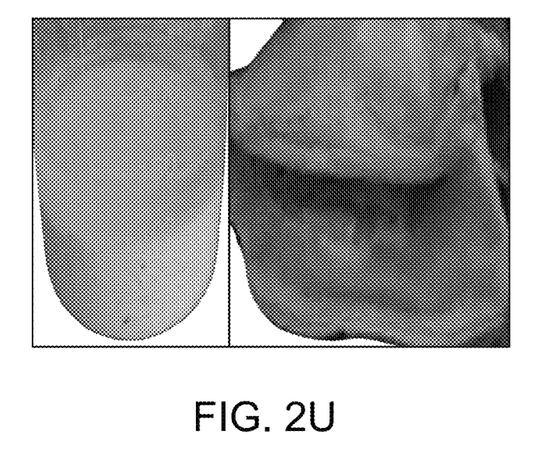
FIG. 2U is an image depicting oyster shell and acid hydrolysis, according to certain embodiments.
Figure 2V:
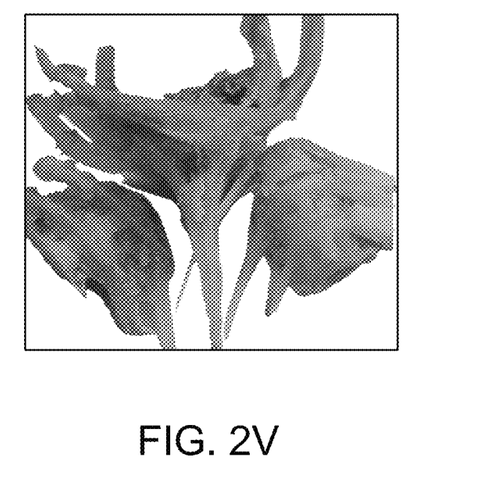
FIG. 2V is an image depicting fishbone, according to certain embodiments.
Figure 2W:
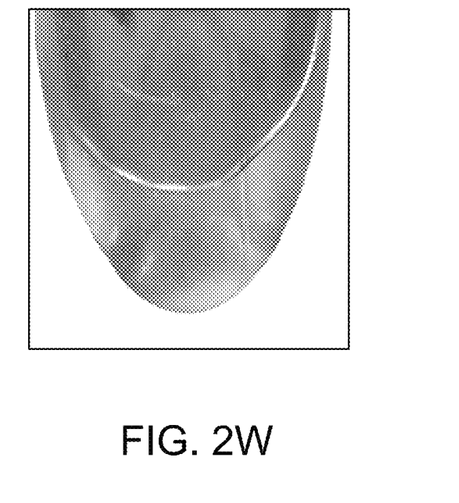
FIG. 2W is an image depicting fish bone acid hydrolysis, according to certain embodiments.
Figure 2X:
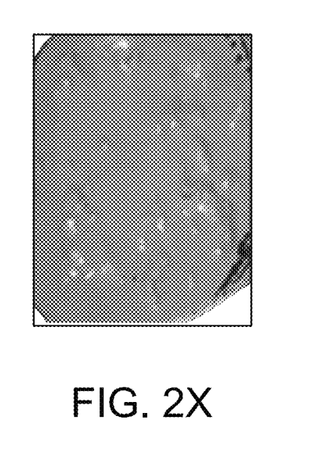
FIG. 2X is an image depicting nanocomposite biomaterials, according to certain embodiments.
Figure 3A:
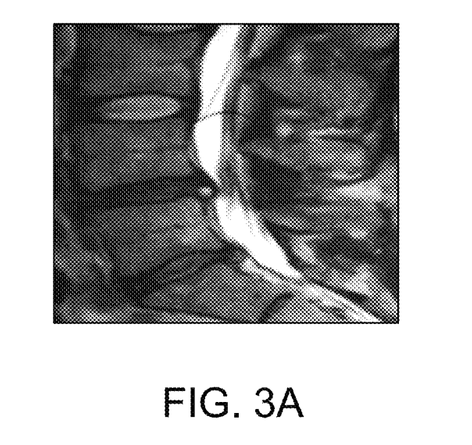
FIG. 3A is an image depicting the human backbone, according to certain embodiments.
Figure 3B:
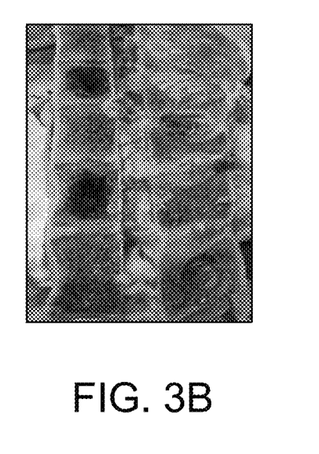
FIG. 3B is an image depicting the damaged backbone of sheep, according to certain embodiments.
Figure 3C:
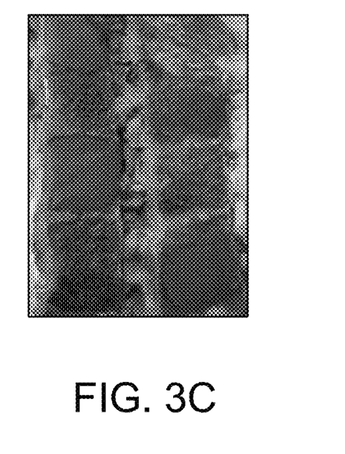
FIG. 3C is an image depicting damaged bone filled by nanocomposite, according to certain embodiments.

The present disclosure outlines the production of a nanostarch and nanocellulose-based organic nutritive nanocomposite bone cement biomaterial, as shown in FIGS. 2A-2X, which may be utilized for the reconstruction or regrowth of damaged bones and joints, as shown in FIGS. 3A-3C. The material is made by combining animal bone powder (minerals) with organic substances, along with organic dyes such as anthocyanin and carotenoid, which serve as antioxidants, following bioprocessing and pyrolysis technologies. The organic nutritive nanocomposite disc or bone biomaterial may replace synthetic materials, as it is organic, biodegradable, and nontoxic to surrounding bone or body tissue. Additionally, it may function as a cell growth medium after being used for replacement.

Numerous modifications and variations of the present disclosure are possible in light of the above teachings. It is therefore to be understood that within the scope of the appended claims, the invention may be practiced otherwise than as specifically described herein.

The invention claimed is:

1. An organic bone and joint replacement biomaterial, comprising:
a nanocomposite comprising a mixture of nanocellulose and nanostarch obtained from date seed, durum seed coat, moringa seed, fish bone, sheep jawbone, and olive seed;
an antioxidant comprising a beet root dye, an ajwa date pigment, a blueberry dye, a black cumin seed pigment, and a velvet apple peel dye,
an organic adhesive selected from the group consisting of *Acacia arabica* gel, agar gel media, and a moringa leaf extract;
an organic composition comprising arrowroot starch gel, pomegranate seed starch, and an animal-based glycerin;
an adhesive composition comprising an okra gel, a cyanoacrylate adhesive, an aloe vera gel, a jackfruit latex, a wood apple glue, a *Lannea* sp. glue, and an aroid root gum;
at least one plasticizer; and
calcium oxide (CaO).

2. The organic bone and joint replacement biomaterial of claim 1, wherein the nanocellulose is present in the nanocomposite in an amount of 45 to 65 wt. % relative to a total weight of the nanocomposite.

3. The organic bone and joint replacement biomaterial of claim 1, wherein the nanocomposite comprises the nanostarch in an amount of 30 to 55 wt. % relative to a total weight of the nanocomposite.

4. The organic bone and joint replacement biomaterial of claim 1, wherein the nanocomposite comprises the nanocellulose having an average particle size of 20 nm or less.

5. The organic bone and joint replacement biomaterial of claim 1, wherein the nanocomposite comprises the nanostarch having an average particle size of 18 nm or less.

6. The organic bone and joint replacement biomaterial of claim 1, having an anthocyanin content of 95 to 110 mg per 100 g of the organic bone and joint replacement biomaterial.

7. The organic bone and joint replacement biomaterial of claim 1, having a carotene content of 1 to 10 mg per gram of the organic bone and joint replacement biomaterial.

8. The organic bone and joint replacement biomaterial of claim 1, wherein the plasticizer is at least one selected from the group consisting of diethylhexyl phthalate, diisononyl phthalate, diisodecylphthalate, dioctyl adipate, tris(2-ethylhexyl)trimellitate, and polyvinyl chloride.

9. The organic bone and joint replacement biomaterial of claim 1, having a calcium content of 5 to 15 parts per million (ppm) relative to a total weight of the organic bone and joint replacement biomaterial.

10. The organic bone and joint replacement biomaterial of claim 1, further comprising at least one acrylate selected from the group consisting of methyl methacrylate, ethyl acrylate, poly(methyl methacrylate), poly(methyl acrylate), polyacrylamide, polyacrylonitrile, poly(acrylic acid), trimethylolpropane triacrylate, hexandiol diacrylate, and pentaerythritol tetraacrylate.

11. The organic bone and joint replacement biomaterial of claim 1, wherein the CaO is present in an amount of 1 to 6 wt. % relative to a total weight of the organic bone and joint replacement biomaterial.

12. The organic bone and joint replacement biomaterial of claim 1, wherein the plasticizer is polyvinyl chloride.

13. The organic bone and joint replacement biomaterial of claim 1, further comprising poly(methyl methacrylate).

14. The organic bone and joint replacement biomaterial of claim 1, wherein the plasticizer is present in an amount of 1 to 10 wt. % relative to a total weight of the organic bone and joint replacement biomaterial.

15. A method of producing the organic bone and joint replacement biomaterial of claim 1, comprising:
hydrolyzing a mixture of date seed, durum seed coat, moringa seed, fish bone, sheep jawbone, and olive seed with at least one inorganic acid to obtain the nanocomposite;
combining the nanocomposite with the organic composition, the organic adhesive, the adhesive composition, the CaO, and the plasticizer to form the organic bone and joint replacement biomaterial; and
pressing the organic bone and joint replacement biomaterial into a mold and curing to form a bone or joint replacement.

16. The method of claim 15, wherein the inorganic acid is at least one selected from the group consisting of hydrochloric acid, nitric acid, hydrobromic acid, sulfuric acid, hydrofluoric acid, and phosphorous acid.

17. The method of claim 15, wherein the inorganic acid is hydrochloric acid, sulfuric acid, and nitric acid.

18. The method of claim 15, further comprising:
drying the date seed, durum seed coat, moringa seed, fish bone, sheep jawbone, and olive seed at a temperature of 125 to 145° C. for 1 to 4 h to obtain a powder comprising olive seed, date seed, moringa seed, fish bone, and sheep jawbone.

19. The method of claim 13, wherein the curing is photocuring or thermal curing.

20. The method of claim 13, wherein the curing includes heating at a temperature of 100 to 160° C. for 3 to 6 h.

\* \* \* \* \*